United States Patent [19]

Sato et al.

[11] 4,200,511

[45] Apr. 29, 1980

[54] DEVICE FOR ELECTROCHEMICALLY MEASURING THE CONCENTRATION OF OXYGEN IN COMBUSTION GASES

[75] Inventors: Kanemasa Sato; Sadayasu Ueno, both of Katsuta; Norio Ichikawa, Mito, all of Japan

[73] Assignee: Hitachi, Ltd., Japan

[21] Appl. No.: 909,520

[22] Filed: May 25, 1978

[30] Foreign Application Priority Data

May 27, 1977 [JP] Japan .................. 52/61188

[51] Int. Cl.² .......................................... G01N 27/46
[52] U.S. Cl. ................................ 204/195 S
[58] Field of Search ..................... 204/195 S

[56] References Cited

U.S. PATENT DOCUMENTS

| B 843,038 | 2/1976 | Sandler | 204/195 S |
|---|---|---|---|
| 3,546,086 | 12/1970 | Sayles | 204/195 S |
| 3,598,711 | 8/1971 | Flais | 204/195 S |
| 3,738,341 | 6/1973 | Loos | 204/195 S |
| 3,841,987 | 10/1974 | Friese et al. | 204/195 S |
| 3,847,778 | 11/1974 | Riddel | 204/195 S |
| 3,960,693 | 6/1976 | Weyl et al. | 204/195 S |
| 4,057,477 | 11/1977 | Weyl et al. | 204/195 S |
| 4,105,524 | 8/1978 | Fujishiro et al. | 204/195 S |

*Primary Examiner*—T. Tung
*Attorney, Agent, or Firm*—Craig and Antonelli

[57] ABSTRACT

A first cylindrical member formed of an ion-conducting solid electrolyte is sealed at one end thereof by a discal plate and inserted at the other end thereof into an axial central bore, formed in a supporting member, in such a manner that the other end of the first cylindrical member is in airtight contact with an offset portion formed in an inner wall surface of the supporting member defining the axial central bore. The first cylindrical member has a first electrode formed on its inner wall surface and a second electrode formed on its outer wall surface. First and second conductors are formed at upper end portions of the first and second electrodes respectively. A second cylindrical member closed at its bottom and housing therein the first cylindrical member in enclosing relationship supports the latter at its bottom and is rigidly secured at its upper end to the supporting member. The second cylindrical member is formed in its wall with a multitude of openings for supplying combustion gases to the exterior of the first cylindrical member. A first terminal member formed therein with an axial central bore is fitted in the axial central bore in the supporting member, so that atmosphere is supplied through the axial central bore in the first terminal member to the interior of the first cylindrical member. A second terminal member formed of a platinum ribbon is connected to the second conductor.

13 Claims, 2 Drawing Figures

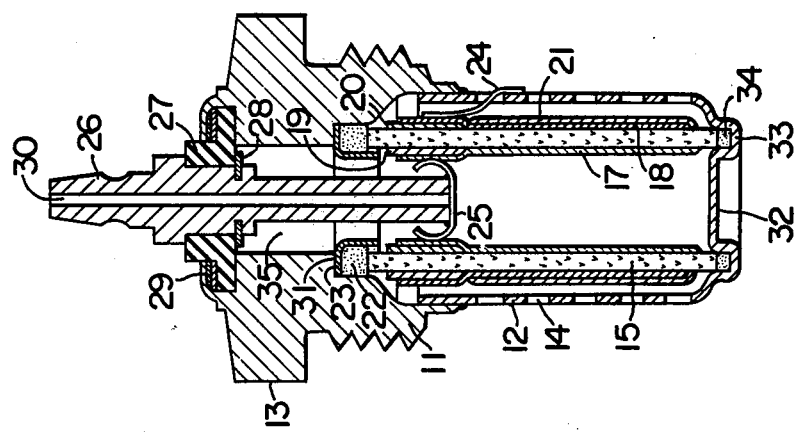
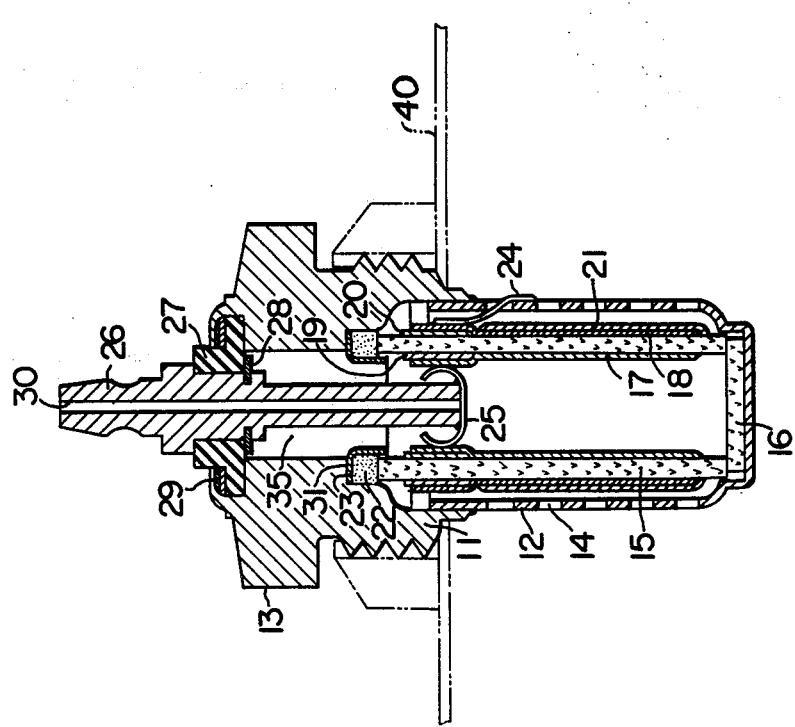

DEVICE FOR ELECTROCHEMICALLY MEASURING THE CONCENTRATION OF OXYGEN IN COMBUSTION GASES

BACKGROUND OF THE INVENTION

This invention relates to a device for electrochemically measuring the concentration of oxygen in combustion gases which uses an ion-conducting solid electrolyte and more particularly to an improvement in the construction of an ion-conducting solid electrolyte member for such device.

It is known that an ion-conducting solid electrolyte member produced by firing zirconia ($ZrO_2$), for example, can have application in a device for electrochemically measuring the concentration of oxygen in combustion gases.

A device of the type described which uses an ion-conducting solid electrolyte member is shown in U.S. Pat. No. 3,960,693, for example.

Heretofore, it has been common practice to produce an ion-conducting solid electrolyte member by forming zirconia or other raw material, as by rubber press forming, into a sack-like tubular shape which is successively subjected to baking, machining and firing. The ion-conducting solid electrolyte member produced in this way is formed with electrodes on its outer and inner surfaces.

In producing an ion-conducting solid electrolyte member by the aforementioned method of the prior art, it is impossible to produce an element of the sack-like tubular shape having a wall thickness of high precision merely by subjecting zirconia or other material to rubber press forming and machining the element produced in this way.

Highly advanced skills are required for forming electrodes of a uniform thickness on the inner and outer surfaces of the element by means of a brush or spraying.

When electrodes are formed by using the techniques of forming a thin layer in vacuum including sputtering, ion plating and vaporization deposition, it is necessary to form the electrodes on the inner and outer surfaces of the element in separate operations. Since the element is of the sack-like tubular shape, the electrode formed on the outer surface of the element tends to have a greater thickness in portions thereof which are nearer to the forward end of the element of the sack-like tubular shape. Conversely, the electrode formed on the inner surface of the element tends to have a greater thickness in portions thereof which are nearer to the flange of the element of the sack-like tubular shape.

Thus a device of the prior art for electrochemically measuring the concentration of oxygen in combustion gases has had the disadvantage that if the formation of electrodes in the ion-conducting solid electrolyte member is not carried out satisfactorily it is impossible to take out an output signal from such member which represents an actual value of the concentration of oxygen.

SUMMARY OF THE INVENTION

An object of this invention is to provide a device for electrochemically measuring the concentration of oxygen in combustion gases which is simple in construction and reliable in performance.

Another object is to provide a device of the type described having an ion-conducting solid electrolyte member which can be readily produced.

Still another object is to provide a device of the type described which is capable of positively transmitting an output signal of its ion-conducting solid electrolyte member.

A further object is to provide a device of the type described which is highly responsive to an output signal.

According to the invention, the ion-conducting solid electrolyte member is constructed in the form of a cylindrical member having open opposite ends, and such cylindrical member is sealed at one end thereof by a discal plate. The cylindrical member having open opposite ends can be obtained by cutting, into a desired length, a cylindrical tube formed as by extrusion molding. Since such cylindrical tube can be produced with a high degree of precision, there is no need to machine such tube as has hitherto been necessary. The element produced in this way is generally fired. It is not required to form electrodes on inner and outer surfaces of the element in separate operations. The production steps followed are such that it is possible to readily form electrodes of a uniform thickness. By sealing one open end of the cylindrical tube with a discal plate following the formation of the electrodes thereon, it is possible to produce an ion-conducting solid electrolyte member of precise finishes. Accordingly, a device for electrochemically measuring oxygen in combustion gases which includes the ion-conducting solid electrolyte member produced as aforesaid is capable of providing a correct value of the concentration of oxygen.

BRIEF DESCRIPTION OF THE DRAWINGS

FIG. 1 is a vertical sectional view of the device for electrochemically measuring the concentration of oxygen in combustion gases which comprises one embodiment of the invention; and FIG. 2 is a vertical sectional view of the device of the type described which comprises another embodiment of the invention.

DESCRIPTION OF THE PREFERRED EMBODIMENTS

FIG. 1 is a sectional view of one embodiment of the device for electrochemically measuring the concentration of oxygen in combustion gases in conformity with this invention. As shown, a first cylindrical member 15 which is formed of an ion-conducting solid electrolyte is an open-ended member of a tubular shape having open opposite ends. The member 15 may be produced by blending zirconia ($ZrO_2$) with yttria ($Y_2O_3$), for example, to provide a stable raw material which is formed into a pipe shape after being granulated by means of a spray dryer or the like. The member 15 has its lower open end, which is exposed to combustion gases, sealed by a discal plate 16 serving as a closure member, which is formed of the same material as the member 15. In bonding the discal plate 16 to the member 15, a zirconia paste of the same material as the member 15 and discal plate 16 is applied to the joints, and the discal plate 16 is brought into intimate contact with the member 15 and fired at a high temperature of 1500° to 1700° C. while caution is exercised against possible displacement of the discal plate 16. The member 15 has its upper open end inserted in an axial central bore 35 formed in a supporting member 11. A first electrode 17 and a second electrode 18 are simultaneously formed on inner and outer wall surfaces of the member 15, by depositing platinum as by sputtering or vaporization deposition, respectively.

A first conductor 19 and a second conductor 20 formed of a paste of precious metal are provided in the vicinity of open upper ends of the electrodes 17 and 18 respectively. Preferably, the first and second conductors 19 and 20 are formed of Pd-Ag, Pt-Au, Pd, Pt, Pt-Pd-Au or platinum alloys. In forming conductors 19 and 20, the raw material is turned into a paste which is applied, by means of a brush, screen process printing, etc., to the walls of the member 15 and fired so that it will be baked on the surfaces. The temperature at which the conductors 19 and 20 are fired may vary depending on the raw material used. However, it is in the range between 1100° and 1700° C., and the conductors 19 and 20 are fired simultaneously as the member 15 is fired. The temperature at which the conductors 19 and 20 are fired is much higher than the preheating temperature in the range between 200° and 300° C. at which the member 15 is preheated when the first and second electrodes 17 and 18 are formed by the techniques of forming a thin layer in vacua. Therefore, the conductors 19 and 20 have high bond strength. The first and second conductors 19 and 20 have a thickness which is over 20 microns and much greater than the thickness of layers formed by the techniques of forming a thin layer in vacua. The first and second conductors 19 and 20 have a large thickness, high consistency and low surface resistance, so that they can be positively brought into contact with other member or bonded to other member by melt adhesion. As a result, it is possible to positively transmit, through the first and second conductors 19 and 20, signals from the first and second electrodes 17 and 18 to an outside circuit.

Atmosphere is introduced into the interior of the first cylindrical member 15 and combustion gases are brought into contact with its outer wall surface as subsequently to be described. A protective layer 21 is mounted outside the first cylindrical member 15 to provide protection thereto both mechanically and chemically. The protective layer 21 is a porous layer formed by applying as by metallization an inorganic material, such as alumina ($Al_2O_3$), magnesia spinel ($MgAl_2O_4$), etc., to the outer wall surface of the member 15.

The first cylindrical member 15 is housed in a second cylindrical member 12 which is closed at its bottom. The second cylindrical member 12 has a wall which converges rather sharply near its lower end and then extends vertically again so as to have a smaller diameter portion at its bottom. The discal plate 16 bonded to the first cylindrical member 15 and unitary therewith is supported in the smaller diameter portion at the bottom of the second cylindrical member 12, which is formed in its wall with a multitude of openings 14 through which combustion gases are supplied to the exterior of the first cylindrical member 15.

The first cylindrical member 15 is in contact at its upper open end with an offset portion 31 formed in an inner wall surface of the supporting member 11 defining the axial central bore 35, through a first pulverulent sealing mass 22 comprising a talc and a metal guide 23 which is attached to the supporting member 11 beforehand. By applying a suitable pressure to the smaller diameter portion at the bottom of the second cylindrical member 12, the first pulverulent sealing mass 22 can be pressed to cause collapse thereof, so as to block fluid communication between the supporting member 11 and the first cylindrical member 15. Then the second cylindrical member 12 is joined at its upper open end to the supporting member 11 by welding.

A plate spring 25 formed of a heat resisting material and serving as electric signal outgoing means has a bent portion which is maintained in contact with the first conductor 19 at a predetermined pressure. The plate spring 25 which has a foil of precious metal welded to its upper surface is joined as by welding to one end of a first terminal member 26.

The first terminal member 26 is formed with an axial central bore 30 and arranged concentrically with the supporting member 11. The terminal member 26 extends at the other end thereof outwardly of the axial central bore 35 in the supporting member 11, and has an insulating bush 27 formed as of ceramics and rigidly secured by a stop ring 28 to the outer periphery of its central portion. The insulating bush 27 has a flange which is clamped down at its upper surface by an upper edge of the supporting member 11 through a packing 29. By this arrangement, the first terminal member 26 is capable of taking out the output of the first electrode 17 through the first conductor 19 and heat-resisting plate spring 25 while being insulated from the support member 11. The first terminal 26 which is formed with the axial central bore 30 as aforementioned allows atmosphere to be introduced into the interior of the first cylindrical member 15 through the bore 30.

The second conductor 20 has a second terminal member 24, formed of a platinum ribbon and serving as electric signal outgoing means, which is joined thereto at one end thereof as by spot welding. The second terminal member 24 is withdrawn at the other end thereof through one of the openings 14 and welded to the outer periphery of the second cylindrical member 12. By this arrangement, the electric signal of the second electrode 18 is grounded to a tested member 40 through the second conductor 20, second terminal member 24, second cylindrical member 12 and supporting member 11.

The supporting member 11 includes a hexagonal nut portion 13, and the supporting member 11 includes an externally threaded lower portion, so that by turning the hexagonal nut portion 13 it is possible to fit the device to the tested member 40, such as an exhaust pipe of a motor vehicle.

Atmosphere serving as a reference gas is admitted to the interior of the first cylindrical member 15 through the axial central bore 30 in the first terminal member 26, and a flow of combustion gases passes through the openings 14 in the wall of the second cylindrical member 12 to the exterior of the first cylindrical member 15. Thus the atmosphere comes into contact with the platinum electrode 17 on the inner wall surface of the first cylindrical member 15 which adsorbs oxygen gas and supplies electrons to generate oxygen ions. Meanwhile the platinum electrode 18 in the form of a porous layer like the platinum electrode 17 and formed on the outer wall surface of the member 15 is exposed to $O_2$, CO, $NO_x$, $CO_2$ and HC in the exhaust gases which are subjected to the catalytic action of the platinum electrode 18 and undergo the following reaction:

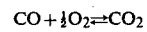

This reaction penetrates the platinum electrode 18 and reaches the surface of the ion-conducting solid electrolyte member 15. As a result, an electromotive force is generated between the two electrodes 17 and 18 in accordance with the difference in the concentration of oxygen between the atmosphere and the exhaust gases. This electromotive force undergoes a sudden change in the vicinity of the theoretical air-fuel ratio, the electromotive force being small when the air-fuel ratio is high and being great when the air-fuel ratio is low. The theoretical air-fuel ratio being 14.7, and the fuel burns in complete combustion when the ratio of the air to the fuel in a mixture has this value. Therefore, it is possible to control the air-fuel ratio on the basis of the electromotive force obtained at the theoretical air-fuel ratio.

According to the present invention discussed hereinabove by referring to one embodiment thereof, the ion-conducting solid electrolyte member 15 is in the form of a cylindrical member open at both ends. This minimizes the production steps and facilitates the production of the member 15. In particular, it is possible to readily produce the ion-conducting solid electrolyte member 15 of small thickness with a high degree of precision. The outer electrode 18 and inner electrode 17 can be formed in one operation in such a manner that they have a uniform thickness. Thus the ion-conducting solid electrolyte member 15 according to the invention has, as compared with a corresponding member of the prior art, the advantages that it is uniform and small in thickness, it is highly responsive because it has a large sensing area, and it generates a stable electromotive force. The electrodes 17 and 18 have the conductors 19 and 20 respectively formed beforehand in one part thereof, and the conductors 19 and 20 are connected to the plate spring 25 and platinum ribbon 24 respectively serving as electric signal outgoing means. By this arrangement, the signals can be positively transmitted. The provision of the conductors 19 and 20 eliminates the need to increase the thickness of the electrodes 17 and 18 more than is necessary and enables the electrodes 17 and 18 to be formed as porous layers formed with a multitude of miniscule pores. As a result, adsorption and ionization of oxygen gas by the electrode 17 functioning as an anode is promoted and the oxidation reaction of HC, CO, etc. in the combustion gases with oxygen gas through the catalytic action of the electrode 18 functioning as a cathode is promoted, so that the ion-conducting solid electrolyte member 15 has improved performance. The ion-conducting solid electrolyte member 15 is supported at opposite ends thereof. It is supported at its lower end by the smaller diameter portion at the bottom of the second cylindrical member 12 serving as a protective sleeve, and at its upper end by the weld produced between the second cylindrical member 12 and the supporting member 11. Thus the member 15 is positively supported. By using the pulverulent sealing mass 22, it is possible to bring the ion-conducting solid electrolyte member 15 into airtight contact with the supporting member 11 by eliminating any gap therebetween. Thus the invention provides a device for electrochemically measuring the concentration of oxygen in combustion gases which is simple in construction and reliable in performance.

FIG. 2 is a vertical sectional view showing another embodiment of the invention. The only difference between the two embodiments lies in the method for closing the ion-conducting solid electrolyte member 15 formed as a cylindrical member having open opposite ends. In FIGS. 1 and 2, like reference characters designate similar parts.

In the embodiment shown in FIG. 2, the second cylindrical member 12 is formed, at its bottom which is not perforated, with an annular channel 33 which surrounds a raised bottom portion 32 disposed inwardly of the protective layer 21. A second pulverulent sealing mass 34 comprising a talc is inserted in the annular channel 33, and then the lower end of the ion-conducting solid electrolyte member 15 in the form of an open-ended cylindrical member is inserted in the annular channel 33 to overlie the sealing mass 34. In fitting the element 15 in the device, the lower end of the element 15 is inserted in the annular channel 33 immediately after the second pulverulent sealing mass 34 is inserted thereinto, and then the upper end of the element 15 is inserted in the offset portion 31 formed in the inner wall surface of the supporting member 11 defining the axial central bore 35. The offset portion 31 has inserted therein the first pulverulent sealing mass 22 held in place by the metal guide 23, so that the upper end of the ion-conducting solid electrolyte member 15 abuts against the sealing mass 22. While the parts are maintained in this condition, pressure is applied to the bottom of the second cylindrical member 12 to cause collapse of the first and second pulverulent sealing masses 22 and 34 to provide an airtight seal to the supporting member 11 and ion-conducting solid electrolyte member 15. Then the upper end of the second cylindrical member 12 is joined by welding to the lower end of the supporting member 11, thereby completing assembling of the parts.

In the embodiment shown in FIG. 2, one end of the ion-conducting solid electrolyte member 15 in the form of a cylindrical open-ended member is sealed by the bottom of the second cylindrical member 12. This enables the upper and lower open ends of the ion-conducting solid electrolyte member 15 to be simultaneously closed in one operation of pressing the member 15 upwardly, thereby markedly reducing the number of operation steps. The embodiment shown in FIG. 2 offers the same effects as the embodiment shown in FIG. 1.

What is claimed is:

1. A device for electrochemically measuring the concentration of oxygen in combustion gases comprising:
   a. a supporting member formed therein with a cylindrical axial central bore;
   b. a first cylindrical member, having inner and outer surfaces, formed of an ion-conducting solid electrolyte, said first cylindrical member being arranged concentrically at one open end thereof in the axial central bore formed in said supporting member and maintained in contact with said supporting member in a portion of an inner wall surface of the latter defining the axial cenral bore so as to block fluid communication between said supporting member and said first cylindrical member, said first cylindrical member being open at both ends;
   c. a first electrode formed on an inner surface of said first cylindrical member;
   d. a second electrode formed on an outer surface of said first cylindrical member;
   e. a first terminal member arranged concentrically in the axial central bore formed in said supporting member and being electrically connected to said first electrode, said first terminal member being formed therein with an axial central bore through which atmosphere can be supplied to the interior of the first cylindrical member;

f. a second terminal member connected to said second electrode;

g. a second cylindrical member having a closed end portion and surrounding said first cylindrical member, said second cylindrical member being arranged concentrically in the axial central bore formed in said supporting member and supported thereby, said second cylindrical member being formed in its wall with a multitude of openings for supplying combustion gases therethrough to the exterior of said first cylindrical member, said closed end portion having a raised bottom portion disposed inwardly of said first cylindrical member; and h. an annular channel formed in said closed end portion of said second cylindrical member having therein the other open end of said first cylindrical member.

2. A device as claimed in claim 1, wherein a pulverulent sealing mass comprising a talc is interposed between said annular channel and said other open end of said first cylindrical member inserted in said annular channel.

3. A device as claimed in claim 1 or 2, wherein a pulverulent sealing mass comprising a talc is interposed between said one open end of said first cylindrical member and the portion of the inner wall surface of said supporting member positioned against said one open end of said first cylindrical member.

4. A device as claimed in claim 1, wherein the diameter of said second cylindrical member decreases near its lower end and then stays constant so as to provide a smaller diameter lower end portion.

5. A device as claimed in claim 1, wherein a protective layer is formed on said second electrode.

6. A device as claimed in claim 1, further comprising:
a. a first conductor formed underneath said first electrode for electrically connecting said first electrode to said first terminal member; and
b. a second conductor formed underneath said second electrode for electrically connecting said second electrode to said second terminal member.

7. A device as claimed in claim 6, wherein said first conductor and said second conductor are formed of one of precious metals and alloys thereof selected from the group consisting of Pd-Ag, Pt-Au, Pd, Pt, Pt-Pd-Au and platinum alloys.

8. A device as claimed in claim 6, including a spring member, made of an electrically conducting material, joined to said first terminal member and contacting said first conductor, for electrically connecting said first conductor to said first terminal member.

9. A device as claimed in claim 1, wherein the first cylindrical member formed of an ion-conducting solid electrolyte is formed by blending zirconia with yttria, granulating the blend, and then forming the resulting product into a pipe shape.

10. A device as claimed in claim 9, wherein the resulting product is formed into a pipe shape by extrusion molding.

11. A device as claimed in claim 1, wherein the closed end portion is not perforated.

12. A device as claimed in claim 1, wherein the first and second electrodes are porous.

13. A device as claimed in claim 1, wherein said first cylindrical member is pipe-shaped.

* * * * *